United States Patent
Do et al.

(10) Patent No.: US 10,869,994 B2
(45) Date of Patent: Dec. 22, 2020

(54) APPARATUSES AND METHODS FOR PROVIDING RADIOPAQUE MEDICAL BALLOONS

(71) Applicants: CLEARSTREAM TECHNOLOGIES LIMITED, Enniscorthy (IE); Hiep Do, Chandler, AZ (US); Andrew Schaffer, Tempe, AZ (US)

(72) Inventors: Hiep Do, Chandler, AZ (US); Andrew Schaffer, Tempe, AZ (US); Paul Fillmore, Tempe, AZ (US)

(73) Assignee: CLEARSTREAM TECHNOLOGIES LIMITED, Enniscorthy County Wexford (IE)

( * ) Notice: Subject to any disclaimer, the term of this patent is extended or adjusted under 35 U.S.C. 154(b) by 560 days.

(21) Appl. No.: 14/915,064

(22) PCT Filed: Aug. 28, 2014

(86) PCT No.: PCT/US2014/053162
§ 371 (c)(1),
(2) Date: Feb. 26, 2016

(87) PCT Pub. No.: WO2015/031616
PCT Pub. Date: Mar. 5, 2015

(65) Prior Publication Data
US 2016/0206861 A1    Jul. 21, 2016

Related U.S. Application Data

(60) Provisional application No. 61/870,913, filed on Aug. 28, 2013.

(51) Int. Cl.
B29C 49/04 (2006.01)
A61M 25/10 (2013.01)
(Continued)

(52) U.S. Cl.
CPC ......... A61M 25/10 (2013.01); B29C 48/0017 (2019.02); B29C 48/0022 (2019.02);
(Continued)

(58) Field of Classification Search
None
See application file for complete search history.

(56) References Cited

U.S. PATENT DOCUMENTS 3,776,794 A * 12/1973 Ingham ................ B29C 47/023
156/143
4,718,897 A    1/1988 Elves
(Continued)

FOREIGN PATENT DOCUMENTS

| CA | 2645531 A1 | 5/2010 |
| JP | S57501165 A | 7/1982 |

(Continued)

OTHER PUBLICATIONS

English Machine Translation of JP2000070375 dated Mar. 7, 2000.
English Machine Translation of JP2008284019A dated Nov. 27, 2008.

*Primary Examiner* — Monica A Huson
(74) *Attorney, Agent, or Firm* — King & Schickli, PLLC

(57) ABSTRACT

A medical balloon is provided for which the working surface may be identified during an interventional procedure with enhanced precision. Related methods of manufacturing such a balloon are also disclosed.

20 Claims, 18 Drawing Sheets

(51) Int. Cl.
  *B29C 51/00*  (2006.01)
  *B29C 48/09*  (2019.01)
  *B29C 48/00*  (2019.01)
  *B29K 105/00*  (2006.01)
  *B29L 31/00*  (2006.01)

(52) U.S. Cl.
  CPC .............. *B29C 48/09* (2019.02); *B29C 49/04* (2013.01); *B29C 51/008* (2013.01); *A61M 2025/1079* (2013.01); *B29K 2105/258* (2013.01); *B29L 2031/7543* (2013.01)

(56) References Cited

U.S. PATENT DOCUMENTS

| | | | | |
|---|---|---|---|---|
| 4,771,778 | A * | 9/1988 | Mar | A61M 25/09033 |
| | | | | 604/103.1 |
| 5,454,788 | A * | 10/1995 | Walker | A61L 29/04 |
| | | | | 604/103 |
| 5,525,388 | A * | 6/1996 | Wand | A61M 25/10 |
| | | | | 138/118 |
| 5,984,963 | A * | 11/1999 | Ryan | A61F 2/93 |
| | | | | 604/265 |
| 6,325,780 | B1 | 12/2001 | Schaible et al. | |
| 6,977,103 | B2 | 12/2005 | Chen et al. | |
| 2001/0043998 | A1 | 11/2001 | Chen et al. | |
| 2002/0099439 | A1* | 7/2002 | Schwartz | A61F 2/2412 |
| | | | | 623/1.24 |
| 2004/0170782 | A1 | 9/2004 | Wang et al. | |
| 2005/0215874 | A1 | 9/2005 | Wang et al. | |
| 2005/0283178 | A1* | 12/2005 | Flagle | A61F 2/95 |
| | | | | 606/191 |
| 2006/0165926 | A1 | 7/2006 | Weber | |
| 2007/0219516 | A1 | 9/2007 | Patel et al. | |
| 2009/0000007 | A1 | 1/2009 | DeMeo | |
| 2009/0299327 | A1 | 12/2009 | Tilson et al. | |
| 2010/0329417 | A1 | 12/2010 | Abe et al. | |
| 2010/0331947 | A1 | 12/2010 | Shalev et al. | |
| 2011/0245912 | A1 | 10/2011 | Shalaby et al. | |

FOREIGN PATENT DOCUMENTS

| | | |
|---|---|---|
| JP | HEI 1990-51556 | 4/1990 |
| JP | 2000070375 A | 3/2000 |
| JP | 2003525092 A | 8/2003 |
| JP | 2007528779 A | 10/2007 |
| JP | 2008515609 A | 5/2008 |
| JP | 2008284019 A | 11/2008 |
| WO | 8200413 A1 | 2/1982 |
| WO | 09604951 A1 | 2/1996 |
| WO | 0134062 A2 | 5/2001 |
| WO | WO200134062 | 5/2001 |
| WO | 03004248 A1 | 1/2003 |
| WO | 2004023980 A2 | 3/2004 |
| WO | 2005107646 A1 | 11/2005 |
| WO | WO2005107646 | 11/2005 |
| WO | WO2006034008 A2 | 3/2006 |
| WO | 2006044637 A2 | 4/2006 |
| WO | 2008030886 A1 | 3/2008 |
| WO | 2010027998 A | 3/2010 |
| WO | 2012047279 A1 | 4/2012 |
| WO | 2012167220 A1 | 12/2012 |
| WO | WO2013134708 A1 | 9/2013 |
| WO | 2013184945 A | 12/2013 |

* cited by examiner

APPARATUSES AND METHODS FOR PROVIDING RADIOPAQUE MEDICAL BALLOONS

This application claims the benefit of U.S. Provisional Patent Application Ser. No. 61/870,913, the disclosure of which is incorporated herein by reference.

TECHNICAL FIELD

This disclosure relates generally to balloons for performing medical procedures, such as angioplasty and, more particularly, to a parison for forming a blow molded medical balloon having a modified portion, such as a layer that is radiopaque, a medical balloon, and related methods.

BACKGROUND OF THE INVENTION

Balloons are routinely used to resolve or address flow restrictions or perhaps even complete blockages in tubular areas of the body, such as arteries or veins. In many clinical situations, the restrictions are caused by hard solids, such as calcified plaque, and require the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

In clinical practice, angioplasty balloons are expanded from a deflated, folded state to an expanded state within a vessel to treat a target area, such as a portion of the circumferential inner wall 1 of a blood vessel V, as shown in FIGS. 1 and 2. The inflation is traditionally completed using an X-ray contrast agent to provide better visibility under X-ray or other form of radiography during the interventional procedure, as illustrated in FIGS. 3 and 3a. Typically, a 70/30 percent mixture of contrast agent and saline is used to inflate the balloon during an angioplasty procedure.

In general, a desirable goal is to reduce inflation and deflation times required for balloons without sacrificing the profile of the balloons, especially for large volume balloons (which can require up to two minutes of inflation/deflation times with the contrast agent). Because of its relatively high viscosity, it would also be desirable to eliminate, or at least reduce the amount of, the contrast agent used in inflation/deflation of the balloons. The use of contrast agent prolongs the inflation/deflation times and also poses the risk of iodine exposure to patients sensitive to iodine. In this regard, a non-radiopaque substance could be used in lieu of the contrast agent, such as for example saline or carbon dioxide, but such substances are invisible during X-ray imaging, and thus do not enhance visibility.

Furthermore, the physician performing the angioplasty procedure should be able to locate the position of the uninflated balloon with accuracy, so that the balloon will be properly positioned once inflated. This is conventionally accomplished by attaching marker bands on the catheter shaft in the region corresponding to the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

Misalignment of the marker bands during placement along the shaft sometimes results in their failure to correspond precisely to the extent of the working surface, as is shown in FIG. 4 (note misalignment amount X between each interior marker band M carried by shaft S and working surface W of balloon 12, which also typically includes a radiopaque tip P at the distal end). Even upon exercising great care to position the markers properly on the underlying shaft in alignment with anticipated boundaries of the working surface when the balloon is inflated, there remains a tendency for mismatch due to several possible factors. One such factor may be the tolerance stack-ups arising as a consequence of the affixation of the balloon to the distal end of the catheter shaft. The balloon also has a tendency to grow in the longitudinal direction when inflated, especially with large and particularly long balloons. Another factor is the tendency of the portion of the catheter shaft within the balloon to bend or flex during inflation. This may lead to misalignment between radiopaque markers fixed to the shaft and the working surface.

Whatever the cause, the resulting misalignment may prevent the clinician from accurately identifying the location of the working surface of the balloon during an interventional procedure. This may lead to a geographic misplacement, or "miss," of the intended contact between the target area T and the working surface W of the balloon 12 (see FIG. 2). It is especially desirable to avoid such an outcome when the balloon is designed to deliver a payload (such as a drug, stent, or both) or a working element to a specified location within the vasculature, since a miss may prolong the procedure (such as, for example, by requiring redeployment of the balloon 12 or the use of another balloon catheter in the case of a drug coated balloon).

Upon deflation, the balloon may also be subject to a phenomenon known as "pancaking." In this condition, the balloon 12 folds down upon itself to a flattened state, as shown in FIG. 5. This situation may cause the balloon to be viewed through fluoroscopy as perhaps still being in the inflated condition, since the full width of the balloon may still be perceived. This can give the clinician the false perception that the balloon remains inflated, when in fact it is not.

Accordingly, the need is identified for a balloon for which the working surface may be identified during an interventional procedure with enhanced precision.

SUMMARY

In one aspect of the disclosure, a method of forming a medical balloon comprises forming a medical balloon having radiopaque and non-radiopaque portion through co-extrusion. For example, the forming step may comprise using a rotating die to form the medical balloon. The forming step may comprise creating a balloon parison using the rotating die. The forming step may also optionally comprise and blow molding the balloon parison into the medical balloon.

Another aspect of the disclosure relates to a medical balloon comprising an inflatable body including a radiopaque felt. The radiopaque felt may be laminated to a wall of the inflatable body. The balloon may include tapered end sections, and the radiopaque felt may correspond to the end sections. The balloon may include a barrel section, and the radiopaque felt may correspond to the barrel section.

A related method of forming the medical balloon described above may comprise applying the radiopaque felt to a tube. The tube may then be extruded to form a parison, which may then be blow molded into the balloon. A related method may also comprise applying the radiopaque felt to a balloon, and then laminating the felt to the balloon.

This disclosure also pertains to a method of providing a medical balloon or a parison for forming a medical balloon with a radiopaque portion. The method may comprise inserting a mandrel and a radiopaque material into the medical balloon or the parison, and expanding the mandrel.

In one embodiment, the radiopaque material comprises a film inserted into the parison prior to the inserting of the mandrel. The method may further include the step of removing the mandrel after the expanding step. The mandrel may be adapted to deposit the radiopaque material on an interior surface of the medical balloon or parison during the expanding step. The mandrel may be partially flexible. The mandrel may comprise expandable interwoven struts. The mandrel may comprise a compliant balloon.

The method may further include the step of blow molding the parison into the medical balloon after the expanding step. The method may further include the step of applying a solution including the radiopaque material to the mandrel prior to the inserting step. The method may comprise the step of expanding the parison to form the medical balloon prior to the inserting and expanding steps.

The radiopaque material may comprise one or more radiopaque fibers associated with the mandrel. The step of expanding the mandrel may be completed to associate the radiopaque fibers with the parison or the medical balloon. The method may also comprise attaching the fibers to an interior surface of the parison or the medical balloon. The attaching may be done using an adhesive.

The radiopaque material may also comprise a lattice, and the method may include associating the lattice with the parison or the medical balloon. The method may comprise inserting the lattice into the parison or balloon using the mandrel. This may be done after the mandrel is compressed.

This disclosure further pertains to an apparatus comprising the combination of a medical balloon or a parison for forming a medical balloon and a mandrel including a radiopaque material and adapted for insertion into and expanding within the medical balloon or the parison.

A related method pertains to providing a parison for forming a medical balloon with a radiopaque portion, comprising inserting a radiopaque material into the parison, and blow molding the parison. The radiopaque material may comprise a film, and further including the step of attaching the film to the parison. The radiopaque material may comprise a lattice, and the method includes associating the lattice with the parison or the medical balloon. The method may also comprise compressing the lattice and then inserting the lattice into the parison or balloon using the mandrel.

This disclosure also relates to a method of providing a parison for forming a medical balloon with a radiopaque portion. The method comprises inserting a radiopaque material comprising a lattice into the parison, and blow molding the parison. The method may further include the steps of compressing the lattice and inserting the lattice into the parison or balloon using the mandrel.

A related aspect of this disclosure is a method of providing a medical balloon or a parison for forming the medical balloon with a radiopaque portion. The method comprises adhering a radiopaque material to an interior surface of the medical balloon or the parison. The adhering step may comprise applying an adhesive to an interior of the medical balloon or the parison, and applying the radiopaque material to the adhesive. The adhering step may comprise applying an adhesive including a radiopaque material to the interior of the balloon or the parison. In any case, the radiopaque material may comprise a powder.

Still another aspect of the disclosure relates to a method of providing a medical balloon or a parison for forming a medical balloon with a radiopaque portion. The method comprises inserting an insert including a radiopaque material into a medical balloon or a parison, and transferring the radiopaque material from the insert to the medical balloon or the parison. The method may further include the step of expanding the insert. The radiopaque material may be applied so as to identify a working surface of the medical balloon, either by defining the edges of the working surface, extending along the working surface, or extending along portions of the balloon other than the working surface.

This disclosure also pertains to a medical balloon or a parison for forming a medical balloon and a mandrel including a lattice comprising a radiopaque material and adapted for insertion into and expanding within the medical balloon or the parison. The lattice may include a longitudinal dimension corresponding to a working surface of the balloon.

Further, the disclosure relates to a medical balloon or a parison for forming a medical balloon and a mandrel including a radiopaque fiber. The mandrel is adapted for insertion into and expanding within the medical balloon or the parison. The mandrel may include a plurality of radially arranged radiopaque fibers.

Yet another aspect of the disclosure relates to a medical balloon comprising an adhesive along an inner lumen and a radiopaque material connected to the balloon by the adhesive. The radiopaque material may be selected from the group consisting of a lattice, a fiber, a powder, and any combination thereof. A mandrel may be provided for carrying the radiopaque material. The adhesive may comprise a radiopaque adhesive.

BRIEF DESCRIPTION OF THE DRAWING FIGURES

Figure 10:
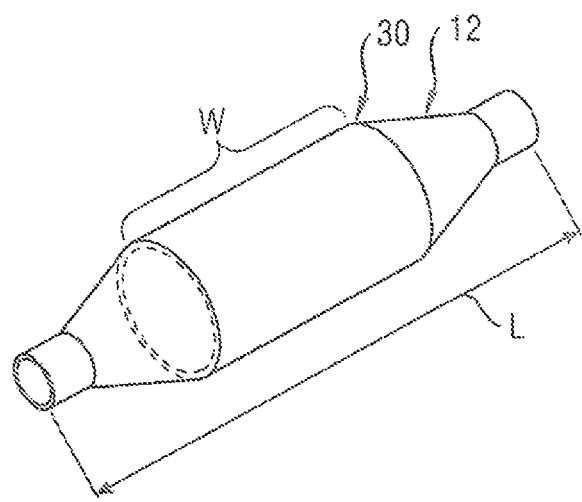
FIG. 10 illustrates a first embodiment according to the disclosure.
Figure 13:
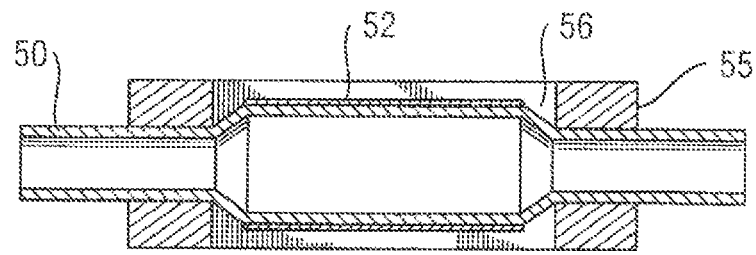
Figure 14:
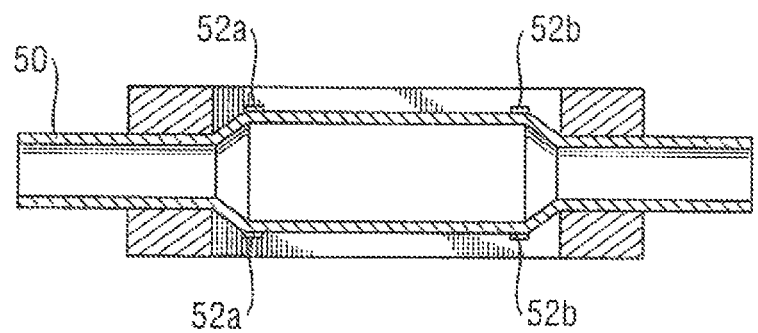
Figure 15:
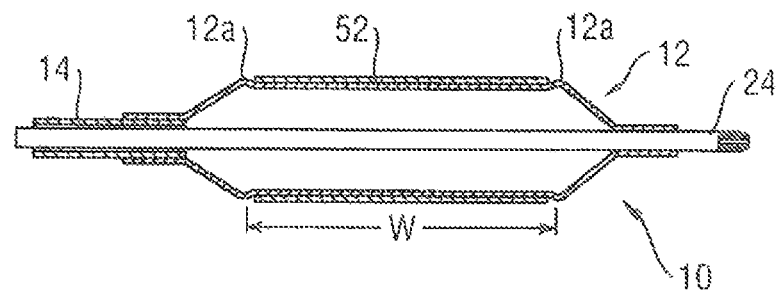
Figure 16:
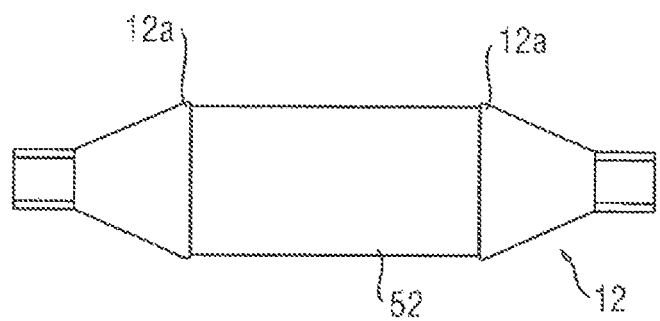
Figure 17:
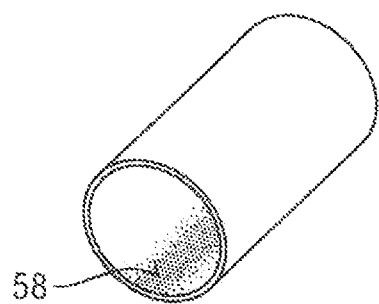
Figure 18:
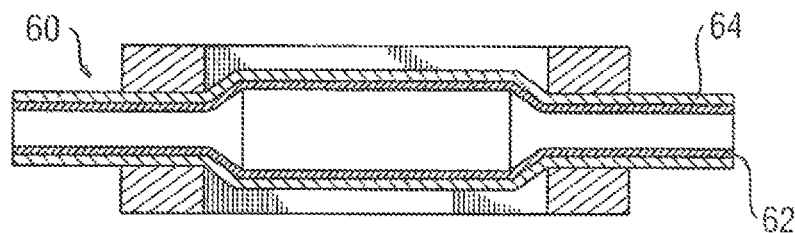
Figures 22, 22A:
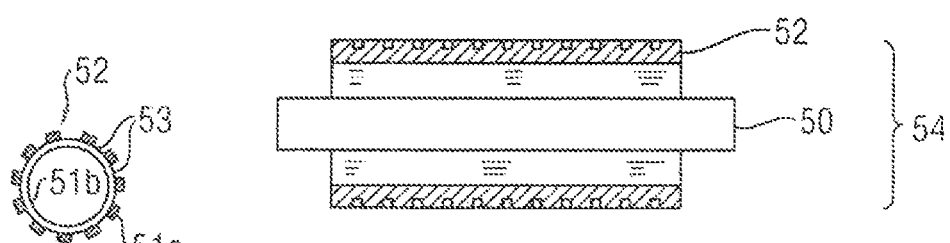
Figure 23:
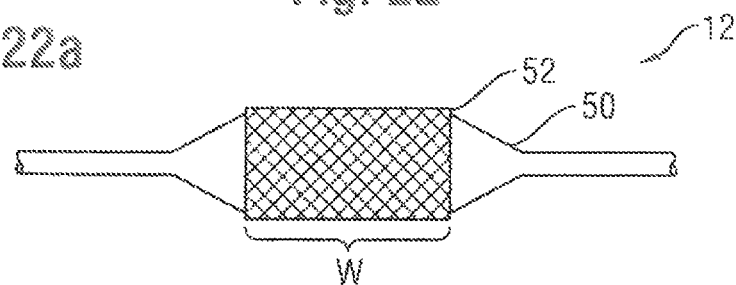
Figure 24:
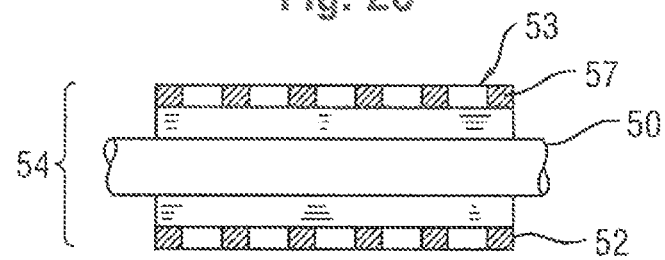
Figure 25:
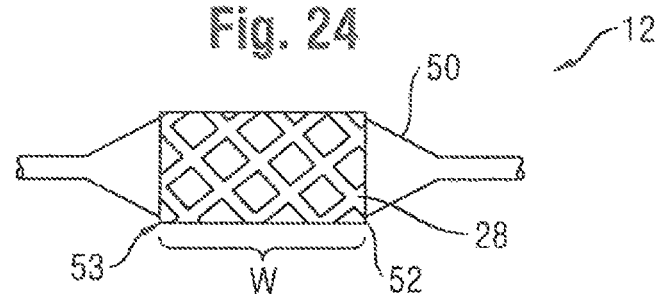
Figure 26:
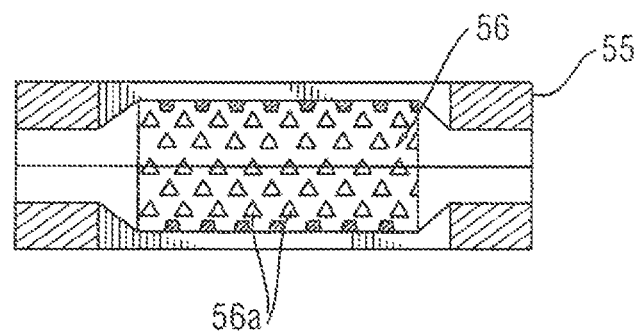

FIGS. 11-11*a* and 12-12*a* show a manufacturing technique for forming the FIG. 10 embodiment;

FIGS. 13 and 14 further shown manufacturing techniques;

FIG. 15 illustrates a further embodiment according to the disclosure;

FIGS. 16 and 17 illustrate another embodiment according to the disclosure;

FIGS. 18-21 show still further embodiments;

FIGS. 22 and 22*a* are cross-sectional side and end views of another embodiment;

FIG. 23 is a side view of a balloon catheter formed according to one aspect of the disclosure;

FIGS. 24 and 25 show a further embodiment;

FIGS. 26-35 show still further embodiments; and

FIGS. 36 to 44 are photographic images illustrating various embodiments.

MODES FOR CARRYING OUT THE INVENTION

The description provided below and in regard to the figures applies to all embodiments unless noted otherwise, and features common to each embodiment are similarly shown and numbered.

Figure 1:
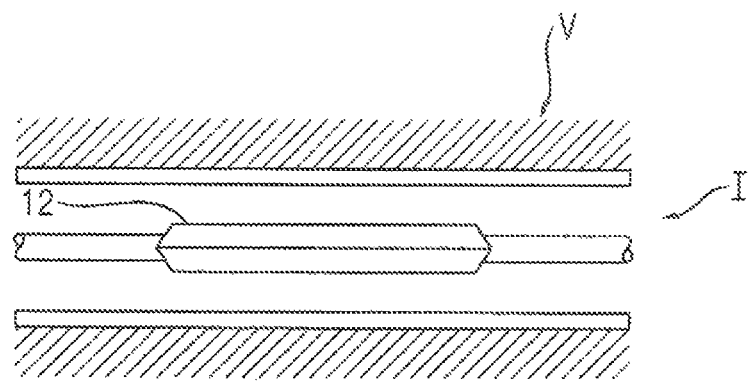
FIGS. 1-9 are illustrative of the background of the invention.
Figure 2:
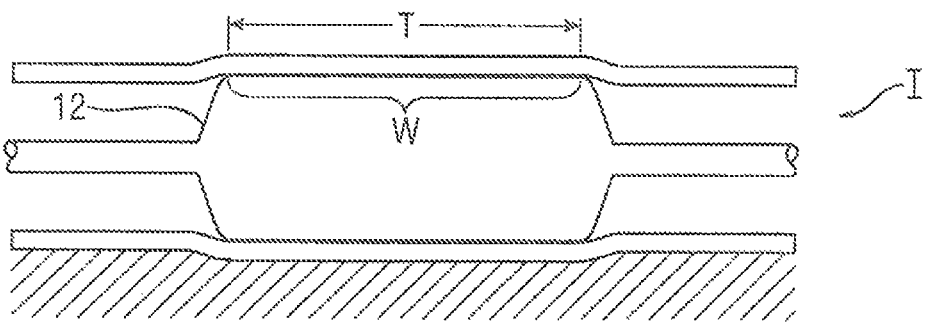
Figure 3:
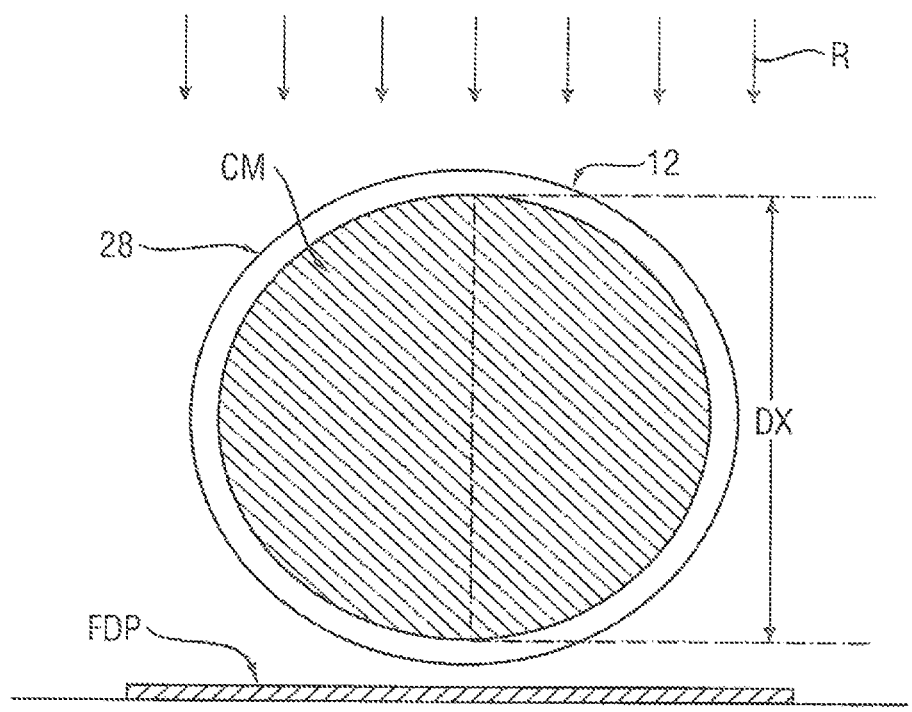
Figure 3A:
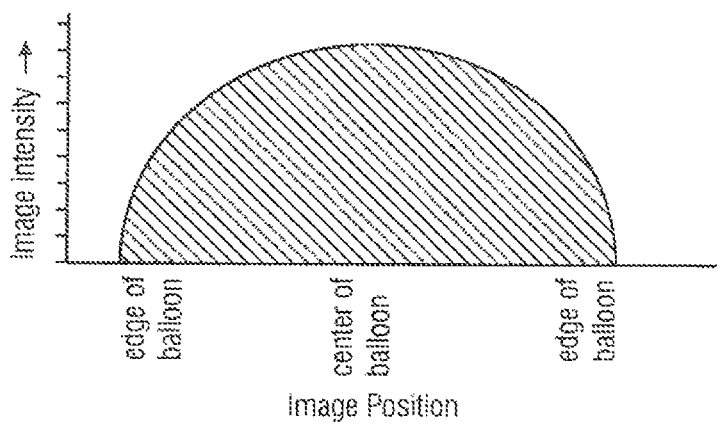
Figure 4:
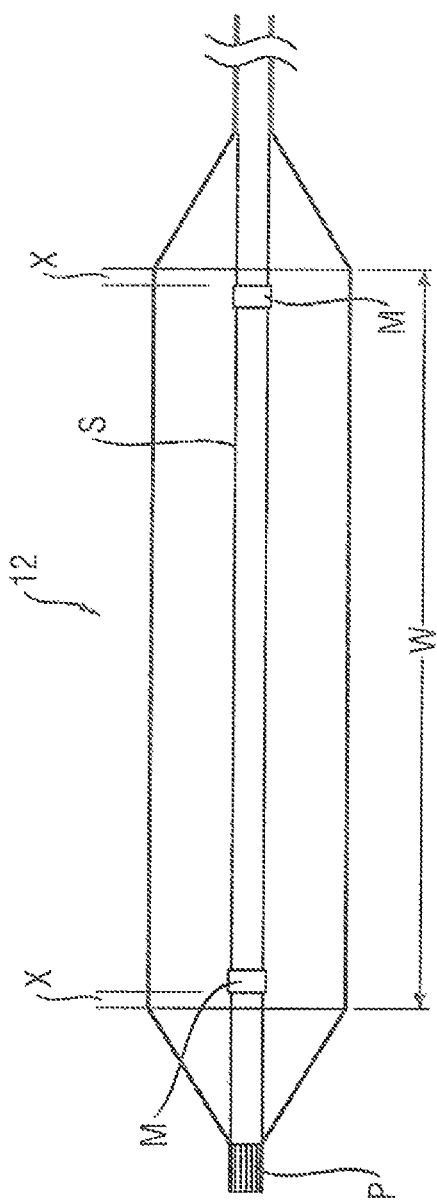
Figure 5:
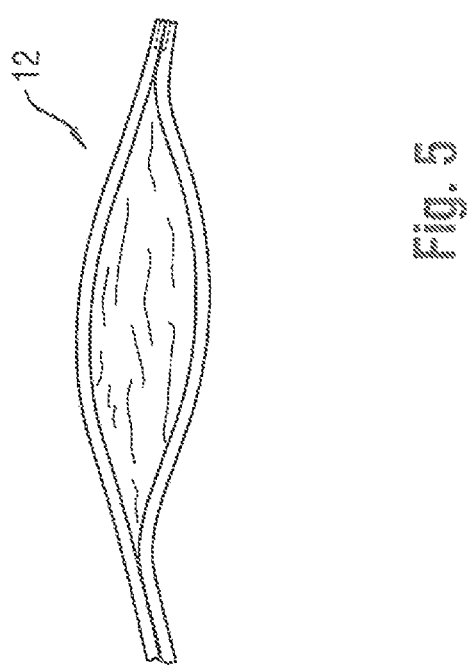
Figure 6:
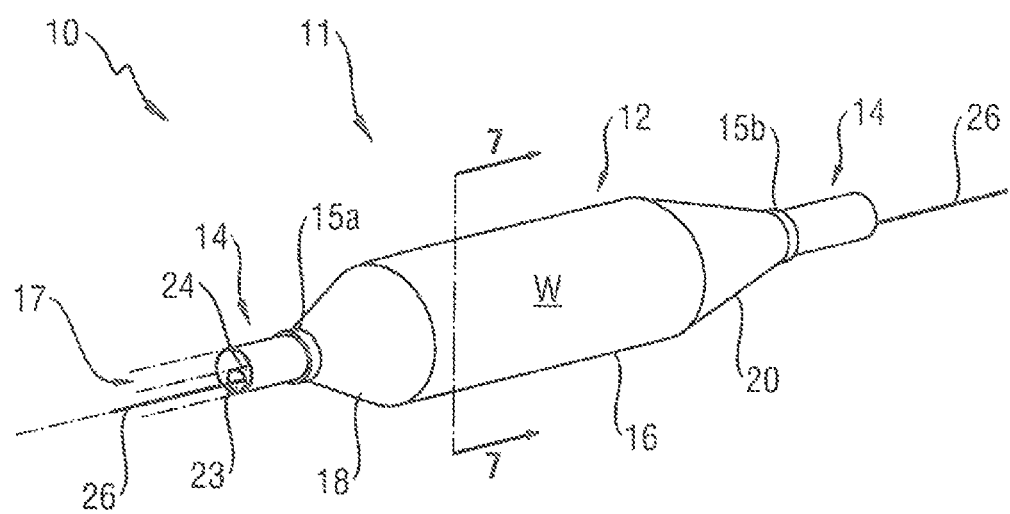
Figure 7:
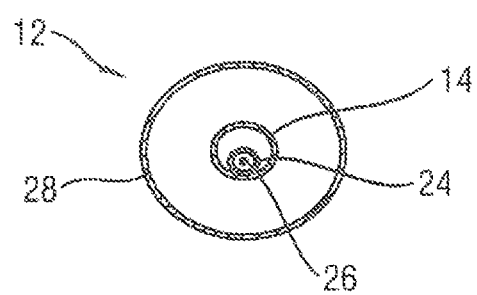
Figure 8:
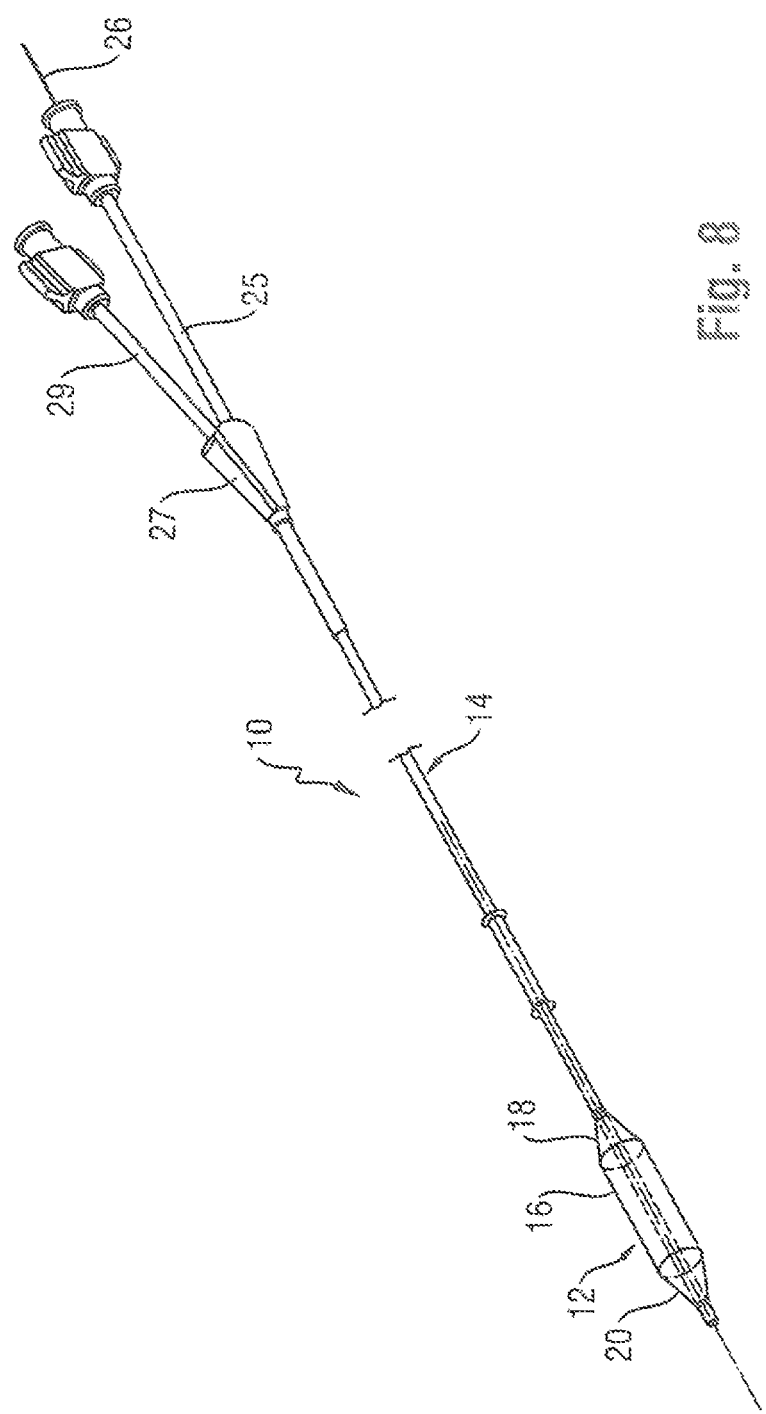

Provided is a catheter 10 having a distal portion 11 with a balloon 12 mounted on a catheter tube 14. Referring to FIGS. 6, 7, and 8, the balloon 12 has an intermediate section 16, or "barrel," and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed at balloon ends (proximal end 15a and distal end 15b) on the cone sections 18, 20 to allow the inflation of the balloon 12 via one or more inflation lumens 17 extending within catheter tube 14 and communicating with the interior of the balloon 12.

Figure 9:
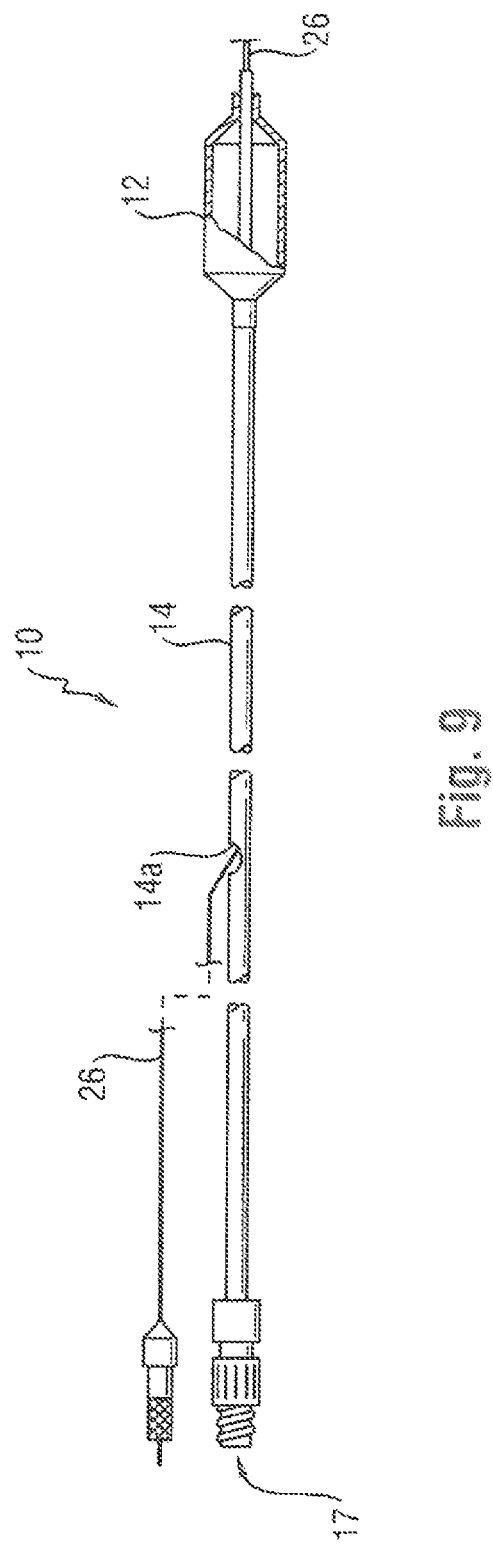

The catheter tube 14 also includes an elongated, tubular shaft 24 forming a guidewire lumen 23 that directs the guidewire 26 through the catheter 10, and along the distal end of which the balloon 12 may be located. As illustrated in FIG. 8, this guidewire 26 may extend through the proximal end of the catheter 10 and a first port 25 of a connector 27 into the lumen 23 to achieve an "over the wire" (OTW) arrangement, but could also be provided in a "rapid exchange" (RX) configuration, in which the guidewire 26 exits a lateral opening 14a closer to the distal end (see FIG. 9) or else is fed through the tip at a passage distally of the balloon 12 ("short" RX; not shown). A second port 29 may also be associated with catheter 10, such as by way of connector 27, for introducing a fluid (e.g., saline, a contrast agent, or both) into the interior compartment of the balloon 12 via the inflation lumen 17.

Balloon 12 may include a single or multi-layered balloon wall 28 forming the interior for receiving the inflation fluid. The balloon 12 may be a non-compliant balloon having a balloon wall 28 that maintains its size and shape in one or more directions when the balloon is inflated. Examples of non-compliant balloons may be found in U.S. Pat. No. 6,746,425 and Publication Nos. US 2006/0085022, US 2006/0085023 and US 2006/0085024, the disclosures of which are hereby incorporated herein by reference. The balloon 12 in such case also has a pre-determined surface area that remains constant during and after inflation, also has a pre-determined length and pre-determined diameter that each, or together, remain constant during and after inflation. However, the balloon 12 could be semi-compliant or compliant instead, depending on the particular use.

In order to provide for enhanced locatability during an interventional procedure, the balloon 12 may have a modified portion having a radiopaque quality. In one embodiment, this radiopaque quality is provided in a manner that allows for a clinician to differentiate, with relative ease and high precision, one portion of the balloon 12 from another (such as, but not limited to, the barrel section 16 including the working surface W from the cone sections 18, 20). This helps the clinician ensure the accurate positioning of the balloon 12 and, in particular, a portion of or the entire working surface W, at a specified treatment location, which may be especially desirable in the delivery of drugs via the balloon working surface W, as outlined in more detail in the following description.

In one embodiment, and with initial reference to FIG. 10, the radiopaque quality is achieved by providing one or more at least partially radiopaque markings 30. The marking or markings 30 may be provided along the balloon 12 to create a defined portion as the working surface W, as contrasted with the full length L of the balloon. For example, a marking 30 may extend along the balloon 12 in a longitudinal direction along the barrel section 16 and over the entire circumference of the working surface W. Alternatively, the marking 30 may extend over only a portion of the working surface W, or may extend over only a different part of the balloon 12 (such as the cone sections 18, 20), as outlined further in the following description.

Figure 11:
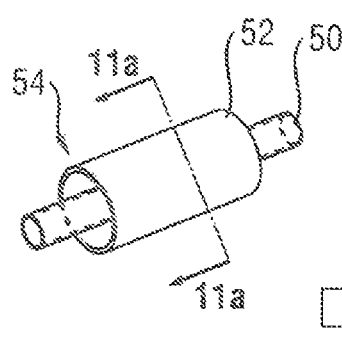
Figure 12:
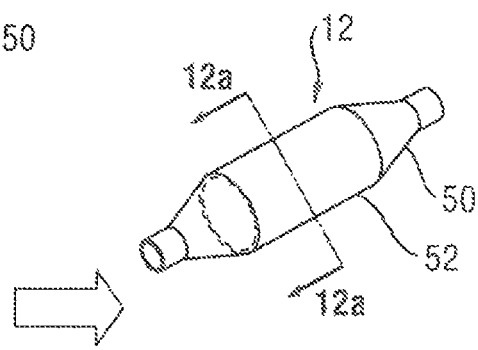
Figure 11A:
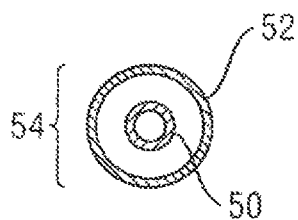
Figure 12A:
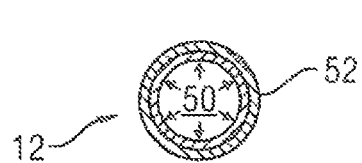

This marking 30 may be provided during a process used to form the balloon 12 having the desired shape created by a multi-layered wall 28. In particular, a first tube 50 comprising a thin layer of material (such as a polymer), may be inserted within a second tube 52, to form a parison 54, as shown in FIGS. 11 (perspective view) and 11a (cross-section). The second tube 52 may also comprise a compatible polymeric material, but could also be formed of a different material (such as metal, including possibly a film). The second tube 52 includes the one or more radiopaque markings 30, which may correspond in length to the barrel section 16 of the finished balloon, as shown in FIG. 11 (but the second tube could extend the entire length of the balloon 12, as discussed below and illustrated by inner tube 62 in FIG. 18). The first, inner tube 50 may then be expanded to form a multi-layered balloon 12 (FIG. 12), with the second, outer tube 52 thus forming a radiopaque outer sleeve, as shown in the cross-sectional view of FIG. 12a.

Turning to FIG. 13, it can be understood that this processing may be achieved using a blow mold 54 having separable portions forming a mold cavity 56 corresponding in shape to the desired shape of the balloon. The outer tube 52 may be pre-positioned in the mold cavity 56, including possibly within a correspondingly shaped recess formed along one or more of the interior surfaces of the mold 55. The inner tube 50 may then be expanded using heat and pressure to form the balloon 12 with the desired shape, and having the outer tube 52 intimately bonded to it.

Figure 19:
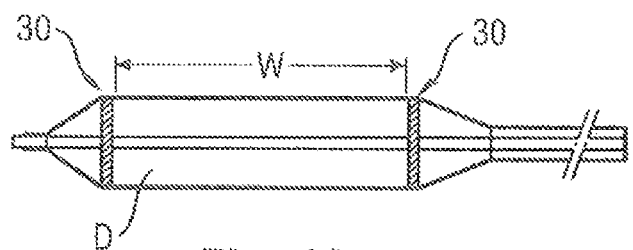

FIG. 14 shows that, instead of a single tube 52, two spaced tubes, such as radiopaque collars 52a, 52b, may be provided on the inner tube 50 in order to provide spaced markings 30 on the finished balloon 12 (see FIG. 19). Like tube 52, these collars 52a, 52b may be pre-positioned in the mold cavity 56 so as to receive the inner tube 50 when inserted. As noted above for tube 52, the collars 52, 52b may be comprised of a thin flexible, material (e.g., a polymer, such as nylon) compatible with the material (e.g., a polymer, such as nylon) of the adjacent layer formed by tube 50, but could also be made of different materials, such as one or more metal foils. Upon expanding the inner tube 50, the collars 52a, 52b are intimately bonded to form a balloon 12 with spaced, radial markers, which as the result of the positioning at predetermined locations in the mold cavity 56 may align precisely with the edges of the working surface W.

The markings 30 may be provided on the tube 52 (or tubes 52a, 52b) in various ways. For example, the markings 30 may be provided by applying a radiopaque material to the tube 52 at the desired location in any shape, pattern or form (including possibly alphanumeric characters to provide information that can be perceived under fluoroscopy, such as a length, diameter, logo, trademark, rated burst pressure, or balloon type). This may be done by inking, spraying, printing, or painting the radiopaque material in fluid form on the surface of the tube 52 (possibly with the application of a mask or the like, in which case the techniques of dipping or rolling in the radiopaque material to form the desired coating could be used). Alternatively, the marking 30 may be embedded in the tube 52, including for example by providing it as part of a film or a felt, or in a bonding agent or adhesive used to bond multiple layers together to form the tube 52 (see, e.g., U.S. Patent Application Publication No. 2011/0160661, the disclosure of which is incorporated herein by reference). The marking 30 may be provided during the process of fabricating the tube 52, such as for example during a co-extrusion process. Examples of such techniques are described in international application PCT/US13/29974, which is incorporated herein by reference.

As perhaps best understood with reference to FIGS. 15 and 16, the mold cavity may be adapted to form the balloon 12 with the desired shape and appearance, and could also be adapted to form shoulders 12a on the balloon 12 once blown. These shoulders 12a may help to retain the outer tube 52 providing the modified portion of the balloon 12 against movement in the longitudinal direction, and thus help to ensure that it remains positioned at the desired location (again, in one embodiment, aligned with the full extent of the working surface W). Additionally or alternatively, as shown in FIG. 17, the inner surface of the outer tube 52 may be adapted for frictionally engaging the outer surface of the tube 50, such as by providing a roughened or textured surface 58.

Additionally or alternatively, an adhesive may be used to improve the bond between the tubes 50, 52. This adhesive may be provided on either tube prior to blow molding. The adhesive may also optionally be provided with a radiopacifier in order to enhance the radiopaque quality of the balloon 12 (see, e.g., U.S. Patent Application Publication No. 2011/0160661).

Another embodiment involves forming the balloon 12 with a modified portion by blow molding a multi-layered parison, wherein at least one of the layers of the parison comprises a radiopaque material. Thus, for example, a parison 60 in this embodiment may include an inner layer comprising a radiopaque film 62, and an outer layer 64 comprising a traditional film that is not made radiopaque by an additive. The blow molding process expands the parison 60 to thus form a balloon 12 having a radiopaque quality corresponding to the length of the inner layer including radiopacifier, which may be the full length L of the balloon 12.

A balloon may be formed by stretching a polymer tube of constant wall thickness to a desired or preferred shape wherein the barrel portion is larger in diameter than other portions intended to be the cones or shoulders of the formed balloon. Such a process may be achieved by placing a balloon parison in to a mold and altering the physical surroundings, such as increasing temperature and/or applying pressure, such as through increased fluid (gas or liquid) pressure, to allow the parison to take the shape of the surrounding mold.

Balloons 12 that incorporate coatings comprising drugs to be applied to the vasculature may also benefit from the above-referenced embodiments. For example, as shown in FIG. 19, a balloon 12 including a defined working surface W, such as by providing radiopaque markings 30 at the transitions between the barrel section 16 and cone sections 18, 20, may include a portion coated with such a drug D, such as one designed for achieving a desired therapeutic effect when applied to the interior of the vessel. The radiopaque marking 30 may also correspond to the location of the drug D on the balloon 12, such as along the entire working surface W or only a portion of it. The drug D may be applied to the inflated balloon as part of the manufacturing process, and prior to folding for insertion in the vasculature. The clinician may thus with the benefit of a fluoroscope determine the precise positioning of the working surface W prior to inflating the balloon 12 in the vasculature to deliver the drug D to the desired location and provide the desired treatment regimen.

Figure 20:
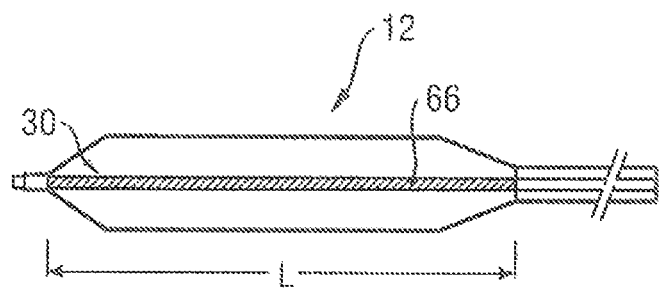
Figure 21:
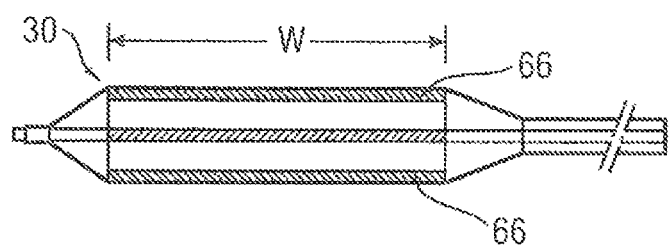

The markings 30 may also be provided as one or more longitudinal strips 66 that do not extend along the entire circumference of the balloon 12, as shown in FIGS. 20 and 21. This may be achieved by providing one or both of the layers 62, 64, or the tube 52, with radiopaque material corresponding to the strips 66, such as by a co-extrusion process. Additional details are provided in PCT/US13/29959, PCT/US13/29967, PCT/EP13/54748, and PCT/US13/29977, the disclosures of each of which are incorporated herein by reference. The presence of plural spaced markings 30 in this manner may also help to distinguish between the inflated condition (in which the markings are spaced), and the properly deflated condition, as the markings would be closer to each other when the balloon is folded.

In another embodiment, the blow molding operation may be arranged to create a balloon 12 with a different type of modified layer. For example, in FIG. 22, an insert 52 may be provided with a functional modification, such as an outer surface that is textured or etched, and associated with an inner tube 50. The insert 52 could be made partially or fully radiopaque if desired (see, e.g., FIG. 10), but such is considered optional. In one embodiment, a multi-layered insert 52 may be provided with an outer radiopaque layer 51a and an inner support layer 51b that is not enhanced with a radiopacifier and exposed by the openings 53 formed by etchings in the outer layer (see FIG. 22a). This may create a particular pattern under fluoroscopy, which may allow for the detection of the locations on the balloon 12 where a drug is present (either on the etched portions or the unetched portions, as desired, which again may correspond to the working surface W).

In any case, on blow molding the resulting parison 54 into a corresponding mold 55 (see FIGS. 13 and 14), a balloon 12 may be formed having an etched or textured outer surface layer 28a of the balloon wall 28. This layer 28a may extend along the entire working surface W, as shown in FIG. 23, or any portion of it. In the case of etching, texturing, or other surface features, the material forming the insert 52 should have a sufficiently high melt flow index such that the features are not caused to disappear as the result of the heat and pressure created during the blow molding process.

Another example for creating a balloon 12 with a modified layer is to provide an insert 52 with one or more openings. For example, as shown in FIG. 24, the insert 52 may be provided as a reticulated or fenestrated body, such as a mesh, screen or lattice having a plurality of crossing members 57 forming openings 53. The body 52 may be tubular in form, as shown, and could comprise more than one piece or part (similar to collars 52a, 52b). As above, the material forming the insert 52 should have a sufficiently high melt flow index such that the features are not caused to disappear as the result of the heat and pressure created during the blow molding process.

When arranged to form a parison 54 and blow molded together, the insert 52 bonds to an inner tube 50 and forms an outer layer of the finished balloon 12. In the case of an insert 52 as shown, the openings 53 expose the balloon wall 28, which may be adapted to form the modified layer (such as by being radiopaque). The body 52 may extend along the entire working surface W, and may optionally be fully or partially radiopaque. Alternatively, the body 52 may be provided with a coating, such as in the form of a drug or an agent providing enhanced lubricity.

It is also possible to modify the mold 55 to provide a surface treatment on the finished balloon 12. For example, as shown in FIG. 25, the inner surfaces of the mold cavity 56 may be provided with a textured pattern 56a, such as by etching, engraving, or the like, so as to form inwardly directed projections. This includes along the portions corresponding to the working surface W of the balloon 12 (e.g., the barrel section). When a parison 54 (which may be a single layer of material), is then expanded in the mold cavity 56 (FIG. 26), the surface of the resulting balloon 12 is provided with a corresponding pattern in the form of an impression of the pattern in the mold 55. In other words, the projections forming the pattern 56a in the mold form depressions in the outer surface of the balloon wall 28.

Figure 27:
Figure 28:
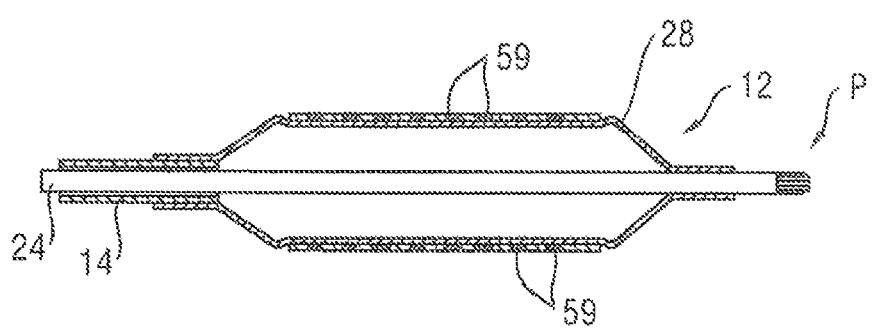
Figure 29:
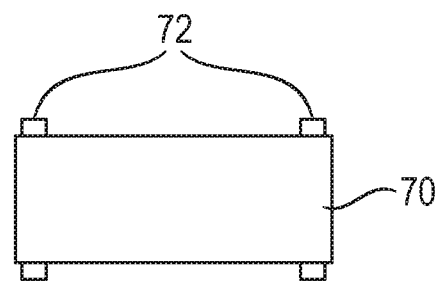

An option in this embodiment is to deposit a material within the mold cavity 56 to partially or completely fill any spaces or gaps formed in the pattern 56a, such as for example a radiopacifier 59. As shown in FIGS. 27 and 28, the balloon 12 resulting from blow molding using a mold 55 with this type of pattern 56a with a filler would thus have a surface layer modified to including the selected filler material (which in the case of a radiopacifier 59 would make the surface partially radiopaque, as shown by the darkened portions of the balloon wall 28 in FIG. 28). The depositing of the material within the mold 55 may be done by injection through an internal passageway opening within the cavity 56, either before or during the molding process, including possibly by spraying the filler material within the mold cavity 56 (such as when the mating portions forming the mold 55 are separated to expose the surface pattern 56a).

The balloon catheter 10 may be formed by forming a balloon parison with discrete radiopaque segments introduced by coextrusion. The coextrusion may involve the use of a rotating die (see, e.g. U.S. Patent Application Publication No. 2003/0100869, the disclosure of which is incorporated herein by reference) to form discrete sections within the tube of one or more materials, such as a radiopaque material. The parison may then be blow molded to form the balloon, with the radiopaque material then embedded in the walls thereof (such as between the ends of the working surface, along the entire working surface, along one or both of the end sections or cones (see, e.g., FIGS. 19-21), and in all cases either partly or fully providing coverage of the respective surfaces).

Figure 30:
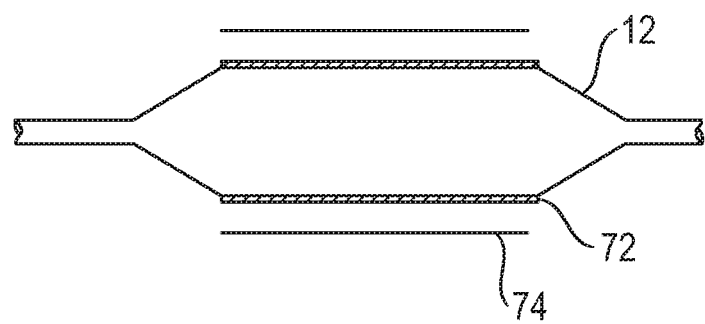
Figure 31:
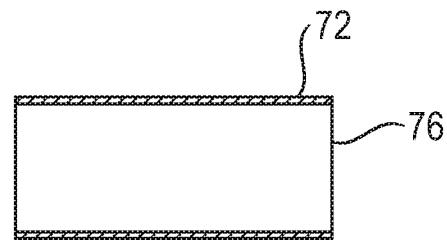

The markings 30 may further by introduced into the balloon 12 through application of a radiopaque felt. For example, attachment of a radiopaque felt 72 to a balloon parison 70 (FIG. 29) may allow for precise identification of each region of the balloon (such as by indicating the portion comprising the working surface relative to other portions). As shown in FIG. 30, the radiopaque felt 72 may also be applied to the exterior of a formed balloon 12, optionally followed by a secondary process, such as lamination (note film 74), to thereby secure the felt in position. Alternatively, as shown in FIG. 31, the radiopaque felt 72 may be applied over an extruded tube 76, followed by a secondary extrusion step, e.g. wire coating, to secure the felt. In such a case, the dual-layer tubing may then be formed into a balloon 12 by steps such as blow-molding or other similar processes known in the art.

Figure 32:
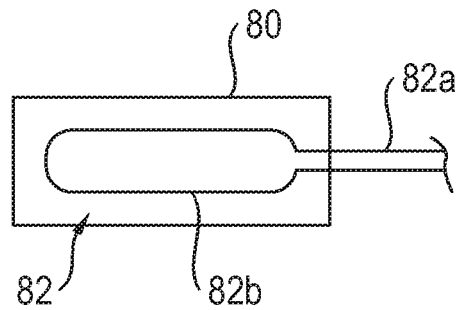

As shown in FIG. 32, radiopaque material may also be applied to an inner lumen of a balloon parison 80 or fully-formed balloon 12 through the use of an expanding mandrel 82. For example, the mandrel 82 may comprise a rigid portion 82a with a distally fixed expandable portion 82b that can have both a retracted configuration and an expanded configuration. The distal section may be sized to efface the inner lumen of the balloon parison 80 when in the expanded configuration, yet still able to pass through both proximal and distal ends thereof in the retracted configuration. The distal end of the mandrel 82 should be constructed of a material that can withstand gas and/or liquid pressure, such as a compliant balloon.

The mandrel 82 may also be comprised of opposed and/or interwoven struts arranged in a manner such that expansion may be achieved during contraction (e.g. a helically wound braid, such as a biaxial braid, wherein reduced angle between the warp and weft at crossing points in turn reduces radial distance between opposing sides) or as opposing struts connected in the middle and at each end are affected by a pivoting joint (e.g. a pantographic mechanism).

The radiopaque material or a portion thereof may also be introduced to the balloon parison prior to molding. For instance, a radiopaque material, such as a film or a felt, that comprises a radiopaque material (e.g. tungsten, barium, tantalum, gold, platinum) with the addition of polymers to provide a structural matrix, as well as optionally stabilizers and/or plasticizers, can be applied to the parison prior to molding. Rolling or folding the radiopaque material allows the material to efface an inner lumen of the parison as it expands following insertion and up to or during a molding step. The addition of an adhesive applied to the exterior of the radiopaque material prior to insertion into the parison may further enhance in adhering the material to the balloon catheter lumen. Those skilled in the art will appreciate that expansion of the distal tip of the mandrel discussed herein will further secure the radiopaque material.

Figure 33:
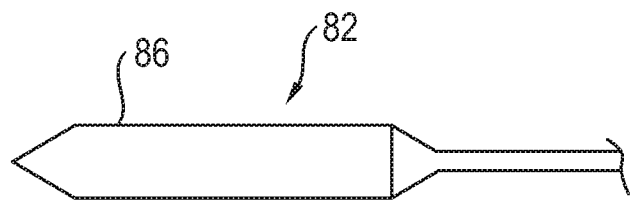

The markings 30 may also be introduced to the balloon 12 as a solution. For example, as indicated in FIG. 33, a solution comprising radiopaque material 86 in suspension optionally aided by stabilizers, may be applied to the outer lumen of the expandable mandrel 82. The distal portion of the expandable mandrel can then be inserted into a balloon parison (e.g., the example provided in FIG. 32) with the mandrel in a retracted configuration (e.g., deflated, in the case of a balloon). The mandrel 82 can then move to the expanded configuration to efface the parison lumen and similarly deposit the solution on the lumen surface, and the parison then used to form the balloon 12. Alternatively, a radiopaque solution may be applied by the expandable mandrel after the balloon is fully formed.

Figure 34:
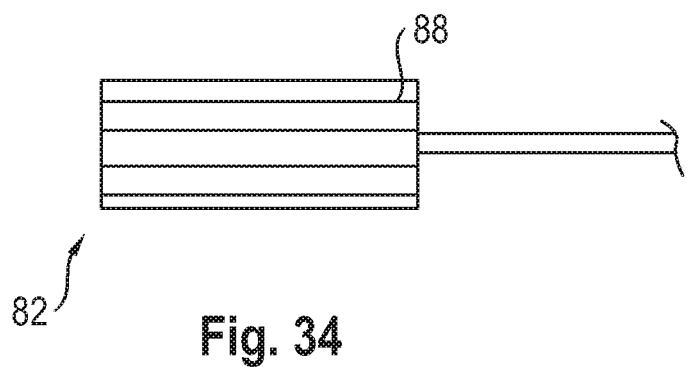

The markings 30 may also comprise radiopaque fibers. Fibers comprised of a radiopaque material, such as tungsten, tantalum, platinum or similar can be achieved through a polymer matrix and optionally formed through an extrusion process. Fibers can then be introduced to the balloon through the use of the expandable mandrel 80 as discussed herein. The mandrel 82 can be sized in such a manner that it can be inserted in through the proximal and distal ends of the balloon parison 80 in the retracted configuration and so that it can fully efface the inner lumen of the parison in the expanded configuration. As shown in FIG. 34, fibers 88 can be arranged in a radial configuration around the mandrel 82 prior to insertion into the parison 80. Following expansion of the mandrel 82, the fibers may be deposited on the inner lumen of the parison 80, after which the mandrel can be reduced to the retracted configuration and withdrawn. Fibers may be adhered to the inner lumen through the use of an adhesive, and optionally later cured during a secondary process, such as exposure to UV light, heat, or flash-off solvents.

Figure 35:
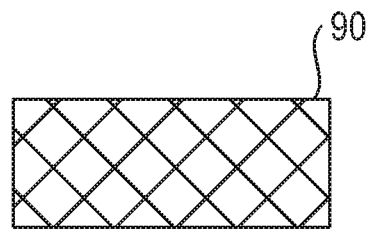

The marking 30 may also be introduced to the balloon 12 as a lattice or matrix 90 of radiopaque material, as shown in FIG. 35. Flexible polymers embedded with radiopaque material may be formed by extrusion, optionally followed by cutting to form the lattice and thus reduce the surface area for increased flexibility. The outer diameter of the lattice or matrix 90 may be sized to efface the inner lumen of a balloon parison 80 and the length of the lattice selected to correspond to the balloon barrel portion or to the cone/shoulder portions. The lattice may be compressed to a smaller diameter to allow for insertion in the parison 80 through the open ends corresponding to the proximal or distal cone regions. An adhesive may further be introduced to assist in anchoring to the inner lumen.

The marking 30 may also be applied to the balloon 12 as a powder. Adhesion of a radiopaque powder may be achieved through selective application of an adhesive to the inner lumen of a parison for forming the balloon. An insert (such as a hypo-tube) may be inserted through one end of a parison, and which insert may be provided with an applicator (e.g., a swab or sponge at the distal end, which may be expandable) to be in communication with the inner lumen. The swab or sponge may then selectively be used to efface the cone portion of the balloon, followed by administration of an adhesive through the insert. Thereby, adhesive is selectively applied to the inner lumen by the sponge. The balloon may then be optionally moved or rotated to enhance even distribution. The insert (hypo-tube) may then be retracted and repeated through the opposing end of the balloon as needed. Following application of the adhesive, radiopaque material (which may be in the form of a powder) may be applied to the inner lumen, and then optionally shaken or rotated. Powder not adhered to the lumen may then be removed prior to introduction of the catheter shaft. Alternatively, a powder may be combined with the adhesive and then applied to the inner lumen through techniques such as brush coating, spray coating or flush and fill.

Example

Radiopaque (RO) powder was weighed in a 20 ml glass vial which then UV light curing adhesive, 208-CTH-F Dymax (Torrington, Conn.) was also added. The percentages of the components were totaled to one hundred percent (100%). The RO coating mixture was thoroughly mixed and transferred to a 3 cc polypropylene syringe which was then placed onto a syringe pump for coating. Attached a nozzle (i.e. EFD needle tip) to the 3 cc syringe and the nozzle was inserted into the lumen diameter of the balloon neck for luminal coating, only the shoulders of the balloon were coated. The infusing rate was set at 0.5 ml/minute. Once the RO coating mixture was pumped up to the shoulder-barrel transition point, it was withdrawn back into the syringe to complete the coating cycle. The coated section was cured using Dymax BlueWave 200 equipment. The coating steps were repeated for the other neck of the balloon.

Below are the X-ray images of different RO materials were used.
Below are the X-ray images of different RO materials were used.

Figure 36:
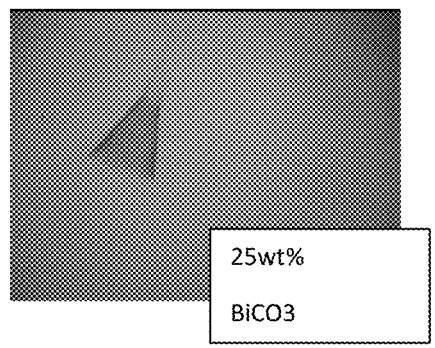
Figure 37:
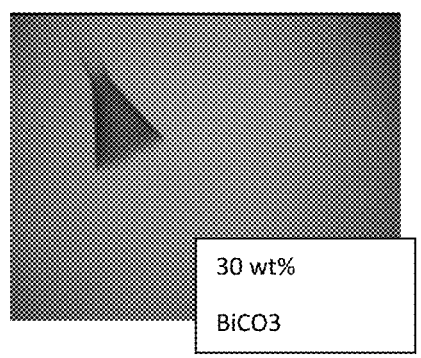
Figure 38:
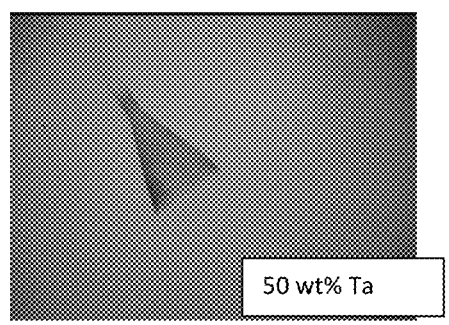
Figure 39:
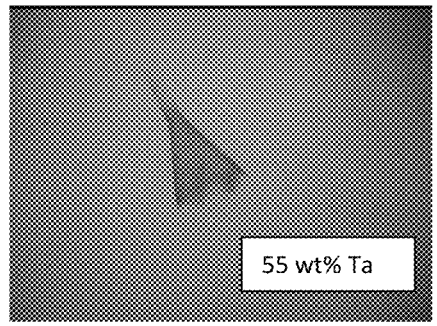
Figure 40:
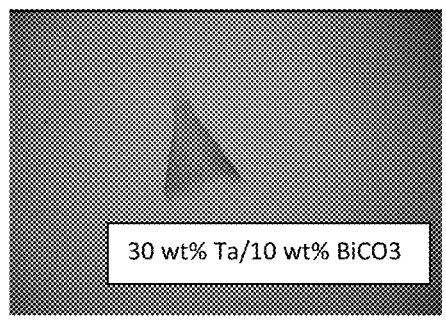
Figure 41:
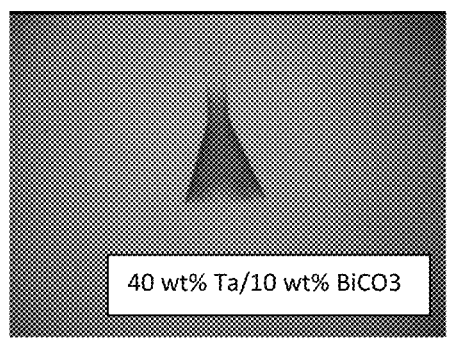
Figure 42:
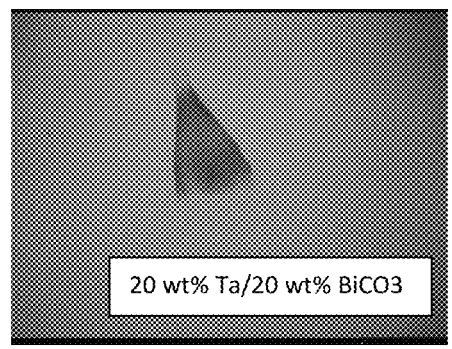
Figure 43:
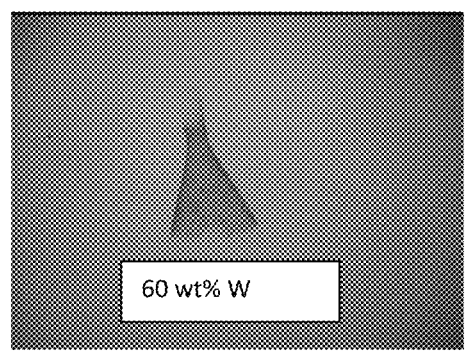
Figure 44:
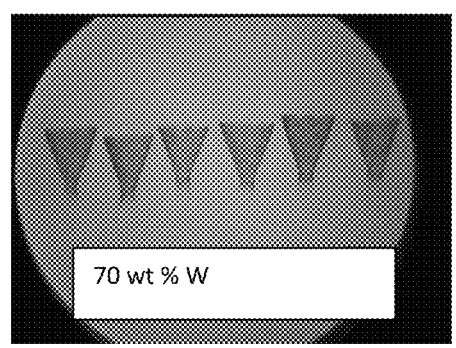

| Description | X-ray (65Kv) | Comments |
| --- | --- | --- |
| Evaluated 20, 30, 35 wt % BiCO3 loadings in 208-CTH-F Dymax. | See FIG. 36 and 37 | 25 wt % RO solution yields flexible coating. 30% and 35 wt % yield harder coating. Optimal cure time for 25% is 4 seconds. Higher loadings yield better X-ray visibility and thicker coating. |
| Evaluated 50 and 55 wt % Ta loadings in 208-CTH-F Dymax. | See FIG. 38 and 39 | 50 wt % Ta solution yields flexible coating. 55 wt % Ta coating yields harder coating. Optimal cure time is 6 seconds. |
| Evaluated combination of Ta and BiCO3 for more flexibible coating with similar or better X-ray visibility. Formulations: 30 wt % Ta/10 wt % BiCO3 40 wt % Ta/10 wt % BiCO3 30 wt % Ta/15 wt % BiCO3 20 wt % Ta/20 wt % BiCO3 | See FIG. 40, 41 and 42 | 30 wt %/10 wt % yields very flexible coating. Other formulations yield harder coating. Optimal cure time is between 6-12 seconds. Higher loading yield better X-ray visibility and thicker coating. |
| Re-evaluated the curing issue of Tungsten loaded formulation. This was found in previous experiments in page 31. | See FIG. 43 | Flexible coating, not completely cured. Three different cure times (6, 12, 18 seconds) were evaluated. Good X-ray visibility. |

Examples of radiopaque materials include, but are not limited to, finely divided tungsten, tantalum, bismuth, bismuth trioxide, bismuth oxychloride, bismuth subcarbonate, other bismuth compounds, barium sulfate, tin, silver, silver compounds, rare earth oxides, and many other substances commonly used for X-ray absorption. The polymer used for making a film, possible with a radiopaque material, may be any polymeric material which can be loaded with radiopacifier and formed into a sufficiently thin film. Examples of polymers include thermoplastic and thermoset polymers. Some examples of thermoplastic polymers include, but are not limited to, polyurethanes, polyamides (nylon 11, nylon 12), polyether-polyamide copolymers such as PEBAX, polyethylene terephthalate or other polyesters, polyvinyl acetate, polyvinyl chloride, and many other thermoplastic materials useful for making films. Some examples of thermoset polymers include, but are not limited to, crosslinked polyurethanes, polyureas, epoxies, acrylics, silicones, and many other thermoset materials that can be formed into thin structures, including films. Any adjacent structures to be bonded, such as tubes 50, 52 or layers 62, 64, may be formed of compatible materials, which may avoid additional processing or the inclusion of a compatibilizer, tie layer or the like.

While the disclosure presents certain embodiments to illustrate the inventive concepts, numerous modifications, alterations, and changes to the described embodiments are possible without departing from the sphere and scope of the present invention, as defined in the appended claims. For example, any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Accordingly, it is intended that the disclosure not be limited to the described embodiments, but that it has the full scope defined by the language of the following claims, and equivalents thereof.

The invention claimed is:
1. A method of providing a medical balloon or a parison for forming a medical balloon with a radiopaque portion, comprising:
   inserting a mandrel and a radiopaque material into the medical balloon or the parison; and
   expanding the mandrel.

2. The method of claim 1, wherein the radiopaque material comprises a film inserted into the parison prior to the inserting of the mandrel.

3. The method of claim 1, further including the step of removing the mandrel after the expanding step.

4. The method of claim 3, wherein the mandrel is adapted to deposit the radiopaque material on an interior surface of the medical balloon or parison during the expanding step.

5. The method of claim 1, wherein the mandrel is partially flexible.

6. The method of claim 1, wherein the mandrel comprises expandable interwoven struts.

7. The method of claim 1, wherein the mandrel comprises a compliant balloon.

8. The method of claim 1, further including the step of blow molding the parison to form a medical balloon after the expanding step.

9. The method of claim 1, further including the step of applying a solution including the radiopaque material to the mandrel prior to the inserting step.

10. The method of claim 1, further including the step of expanding the parison to form the medical balloon prior to the inserting and expanding steps.

11. The method of claim 1, wherein the radiopaque material comprises one or more radiopaque fibers associated with the mandrel, and the step of expanding the mandrel is completed to associate the radiopaque fibers with the parison or the medical balloon.

12. The method of claim 1, wherein the radiopaque material comprises one or more radiopaque fibers, and the method comprises adhesively attaching the fibers to an interior surface of the parison or the medical balloon.

13. The method of claim 1, wherein the radiopaque material comprises one or more radiopaque fibers, and the method comprises adhesively attaching the fibers to the parison or the medical balloon.

14. The method of claim 1, wherein the radiopaque material comprises a lattice.

15. A method of providing a medical balloon or a parison for forming a medical balloon with a radiopaque portion, comprising:
    inserting an inflatable mandrel and a radiopaque material into the medical balloon or the parison; and
    expanding the mandrel.

16. The method of claim 14, further including the step of blow molding the parison to form a medical balloon after the expanding step.

17. The method of claim 14, wherein the mandrel comprises expandable interwoven struts.

18. The method of claim 14, wherein the mandrel comprises a compliant balloon.

19. A method of providing a medical balloon, comprising:
    inserting an inflatable mandrel and a radiopaque material into a parison;
    expanding the mandrel; and
    blow molding the parison into the medical balloon.

20. The method of claim 19, wherein the mandrel is inflatable.

* * * * *